(12) United States Patent
Sato et al.

(10) Patent No.: US 8,642,032 B2
(45) Date of Patent: Feb. 4, 2014

(54) METHOD FOR SCREENING OF PATIENT TO BE ADMINISTERED WITH PHARMACEUTICAL AGENT COMPRISING ANTI-CANCER ANTIBODY AS ACTIVE INGREDIENT

(75) Inventors: Takashi Sato, Shizouka (JP); Naoya Kimoto, Shizuoka (JP); Yuji Ohki, Tokyo (JP); Akiko Furuya, Tokyo (JP); Hiroyuki Ishida, Tokyo (JP); Atsushi Ochiai, Chiba (JP)

(73) Assignees: Kyowa Hakko Kirin Co., Ltd., Tokyo (JP); Japan as Represented by President of National Cancer Center, Tokyo (JP)

( * ) Notice: Subject to any disclaimer, the term of this patent is extended or adjusted under 35 U.S.C. 154(b) by 748 days.

(21) Appl. No.: 12/666,716

(22) PCT Filed: Jun. 26, 2008

(86) PCT No.: PCT/JP2008/061669
§ 371 (c)(1),
(2), (4) Date: Feb. 24, 2010

(87) PCT Pub. No.: WO2009/001904
PCT Pub. Date: Dec. 31, 2008

(65) Prior Publication Data
US 2010/0189724 A1    Jul. 29, 2010

Related U.S. Application Data

(60) Provisional application No. 60/946,278, filed on Jun. 26, 2007.

(51) Int. Cl.
*A61K 39/395* (2006.01)
*C12Q 1/68* (2006.01)
*G01N 33/574* (2006.01)

(52) U.S. Cl.
USPC ............... 424/130.1; 424/138.1; 424/155.1; 424/156.1; 435/6.1; 435/7.23; 436/501

(58) Field of Classification Search
None
See application file for complete search history.

(56) References Cited

FOREIGN PATENT DOCUMENTS

| EP | 1767625 A1 | 3/2007 |
|---|---|---|
| WO | 92/17608 A1 | 10/1992 |
| WO | 94/11401 A1 | 5/1994 |

OTHER PUBLICATIONS

Jesus et al (Acta Cir Bras, 2005, vol. 20, 6 pages).*
Tanaka et al (Br. Journal of Surgery, 2003, vol. 90, pp. 95-101).*
Altundag et al (Medical Hypothesis, 2004, vol. 63, pp. 277-280).*
Ihrie et al, Cell Cycle, 2005, vol. 4, pp. 873-876.*
European Patent Office, Search Report dated Sep. 16, 2011 from the European Patent Office in counterpart European application No. 08777634.0.
Berx et al. "Involvement of Members of the Cadherin Superfamily in Cancer." Cold Spring Harbor Perspectives in Biology, vol. 1:a003129, Sep. 23, 2009, pp. 1-27.
Shen, Jie et al., "Identification and Validation of Differences in Protein Levels in Normal, Premalignant, and Malignant Lung Cells and Tissues Using High-Throughput Western Arrat and Immunohistochemistry", Cancer Research. 2006. pp. 11194-11206.
Green, Steven K. et al., "Disruption of Cell-Cell Adhesion Enhances Antibody-dependant Cellular Cytotoxicity: Implications for Antibody-based Therapeutics of Cancer", Cancer Research. 2002. pp. 6891-6900.
European Search Report issued Jul. 20, 2010, in corresponding European Patent Application No. 08777634.0.
Japanese Patent Office, Communication dated Apr. 16, 2013, issued in a counterpart application No. 2009-520639.

* cited by examiner

*Primary Examiner* — Karen Canella
(74) *Attorney, Agent, or Firm* — Sughrue Mion, PLLC (57) ABSTRACT

The present invention provides a method for screening a patient to be administered with a pharmaceutical composition which comprises an anti-cancer antibody as an active ingredient, said method comprising collecting samples from patients who expresses an antigen which is recognized by the anti-cancer antibody, measuring cadherin function in the samples, and selecting a patient whose the cadherin function is decreased or deleted; a method for screening a patient who has a high efficacy ratio for a pharmaceutical composition which comprises an anti-cancer antibody as an active ingredient; and a method for improving an efficacy ratio for a pharmaceutical composition which comprises an anti-cancer antibody as an active ingredient.

13 Claims, 3 Drawing Sheets

METHOD FOR SCREENING OF PATIENT TO BE ADMINISTERED WITH PHARMACEUTICAL AGENT COMPRISING ANTI-CANCER ANTIBODY AS ACTIVE INGREDIENT

TECHNICAL FIELD

This invention relates to a method for screening a patient to be administered with a pharmaceutical composition which comprises an anti-cancer antibody as an active ingredient, a method for screening a patient who has a high efficacy ratio for a pharmaceutical composition which comprises an anti-cancer antibody as an active ingredient, a method for improving an efficacy ratio for a pharmaceutical composition which comprises an anti-cancer antibody as an active ingredient, and a method for administering a pharmaceutical composition which comprises an anti-cancer antibody as an active ingredient.

BACKGROUND ART

A therapeutic antibody is an agent which comprises an antibody as an active ingredient. An antibody has the property to specifically bind to a specific molecule (antigen) (Non-patent Reference 1).

The therapeutic antibody is useful in treating cancer patients. Currently, an anti-HER 2 antibody Trastuzumab (Herceptin: registered trademark), an anti-EGFR antibody Cetuximab (Erbitux: registered trademark) (Non-patent Reference 1), and the like are on the market.

When a therapeutic antibody is administered to a patient, expression of an antigen on cancer cells is analyzed before administration of the anti-cancer antibody. For the therapeutic antibody to show its effect, it is necessary that the antibody molecule binds to the antigen of cancer cells (Non-patent Reference 1). Accordingly, there are carried out by selecting a patient in which expression of antigen on cancer cells is observed screening, and the therapeutic antibody is administered to the selected patients (Non-patent Reference 2). As a specific example, Hercep Test (registered trademark) before administration of Trastuzumab can be cited. In the Hercep Test, a kit for testing expression of HER 2 as the antigen of Trastuzumab is used, and expression level of HER 2 in a cancer tissue of a patient is measured by an immunohistological staining method (Non-patent. Reference 2). Trastuzumab is administered only to the patient whose expression of HER 2 was found by the Hercep Test (Non-patent Reference 3).

Screening of a patient to be administered with the therapeutic antibody is important from the viewpoint of side effects. In addition, the therapeutic antibody should not be administered to patientsnot predicting in its effectiveness. Cardiac toxicity has been reported as a side effect of Trastuzumab (Non-patent Reference 4), and pimple-like skin erythema or the like has been reported as a side effect of Cetuximab (Non-patent Reference 5).

However, even if a patient is screened based on the presence or absence of the antigen expression, the therapeutic antibody is not necessarily effective in all patients. It has been reported that the objective response rate of Herceptin was 36% in a second phase clinical test carded out on the HER 2 high expression breast cancer patients screened by Hercep Test (Non-patent Reference 6).

E-cadherin is localized on the surface cell membrane, and is involved in the formation and maintenance of cell adhesion (Non-patent Reference 7). E-cadherin does not function by the E-cadherin alone but functions by co-operating with certain molecules (Non-patent Reference 7). Catenin connects E-cadherin with cytoskeleton by binding to the intracellular domain of E-cadherin (Non-patent Reference 7).

Deletion of E-cadherin function is known in cancer patients. As the deletion of E-cadherin function, a case in which the expression level of E-cadherin protein is decreased, a case in which the expression level of a molecule which cooperates with E-cadherin protein is decreased, and the like are known (Non-patent Reference 8). It is known that deletion of expression of E-cadherin protein was found in 14% of gastric cancer patients and, in addition, E-cadherin was not localized on the cell membrane in 48% of patients among the patients in which expression of E-cadherin was found (Non-patent Reference 9).

It has been reported that there is a relation between deletion of E-cadherin function and prognosis of patients (Non-patent Reference 10). For example, there is a report stating that, among prostatic cancer patients to whom radiotherapy or hormone therapy was applied, patients who have low expression level of E-cadherin protein are poor in prognosis in comparison with the patients having normal expression level of E-cadherin protein (Non-patent Reference 10).

It has been reported that survival effect of anti-HLA antibody is enhanced in a mouse model to which a human colon cancer cell line was transplanted, as a result of the neutralization of cadherin function due to administration of an anti-cadherin antibody (Non-patent Reference 11). A possibility was suggested in this report that a medicament which neutralizes cadherin function is useful as an agent for enhancing the effect of therapeutic antibody (Non-patent Reference 11).

However, it is not known that a patient to whom anti-cancer therapeutic antibody is effective can be screened by examining conditions of the original cadherin function in cancer cells.

Non-patent Reference 1: *Nature Reviews Cancer* 2006; 6: 714-27

Non-patent Reference 2: *European Journal of Cancer* 2000; 36: 170-6

Non-patent Reference 3: *Clinical Cancer Research* 2001; 7: 1669-75

Non-patent Reference 4: *British Journal of Cancer* 2006; 94: 1016-20

Non-patent Reference 5: *Journal of Clinical Oncology* 2004; 22: 1201-8

Non-patent Reference 6 *Journal of Clinical Oncology* 2005; 23: 2162-71

Non-patent Reference 7: *Molecular Cell Biology Research Communications* 1999; 2: 77-85

Non-patent Reference 8: *Cancer and Metastasis Review* 1999; 18: 15-30

Non-patent Reference 9: *Annals of Surgery* 2005; 242: 676-83

Non-patent Reference 10: *Cancer Reseach* 1994; 54: 3929-33

Non-patent Reference 11: *Cancer Reseach* 2002; 62: 6891-900

DISCLOSURE OF INVENTION

Problems to be Solved by the Invention

When an anti-cancer therapeutic antibody is administered to a patient, expression of the antigen on cancer cells, which is recognized by the anti-cancer antibody, is analyzed before the administration, in order to estimate an efficacy of the therapeutic antibody. However, even if the therapeutic antibody is administered by screening patients expressing the antigen, the therapeutic antibody is not always successful in such patients. In addition, since the therapeutic antibody is expensive, it is necessary to administer it by screening, in advance, the patients predicting in its effectiveness. Based on the above, there is a demand for a method for screening a patient predicting in effectiveness of anti-cancer therapeutic antibody, before administration of the anti-cancer therapeutic antibody.

Means for Solving the Problems

The present invention relates to the following (1) to (22):
(1) A method for screening a patient to be administered with a pharmaceutical composition which comprises an anti-cancer antibody as an active ingredient, said method comprising collecting samples from patients who expresses an antigen which is recognized by the anti-cancer antibody, measuring cadherin function in the samples, and selecting a patient whose the cadherin function is decreased or deleted;
(2) The method described in the above (1), wherein the cadherin is E-cadherin;
(3) The method described in the above (1) or (2), wherein the patient is a patient with a solid carcinoma;
(4) The method described in any one of the above (1) to (3), wherein the anti-cancer antibody is an antibody against a solid carcinoma;
(5) The method described in any one of the above (1) to (4), wherein the anti-cancer antibody is an anti-PERP antibody;
(6) The method described in any one of the above (1) to (4), wherein the method for measuring cadherin function is a genetic engineering technique or an immunological method;
(7) The method described in the above (6), wherein the immunological method is a method in which an antibody which recognizes cadherin is allowed to react with a sample to thereby measure its reactivity;
(8) A method for screening a patient, who has a high efficacy ratio for a pharmaceutical composition which comprises an anti-cancer antibody as an active ingredient, said method comprising collecting samples from patients who expresses an antigen which is recognized by the anti-cancer antibody, measuring a cadherin function in the samples, and selecting a patient whose the cadherin function is decreased or deleted is selected;
(9) The method described in the above (8), wherein the cadherin is E-cadherin;
(10) The method described in the above (8) or (9), wherein the patient is a patient with a solid carcinoma;
(11) The method described in any one of the above (8) to (10), wherein the anti-cancer antibody is an antibody against a solid carcinoma;
(12) The method described in any one of the above (8) to (11), wherein the anti-cancer antibody is an anti-PERP antibody;
(13) The method described in any one of the above (8) to (12), wherein the method for measuring cadherin function is a genetic engineering technique or an immunological method;
(14) The method described in the above (13), wherein the immunological method is a method in which an antibody which recognizes cadherin is allowed to react with a sample to thereby measure its reactivity;
(15) A method for improving an efficacy ratio for a pharmaceutical composition which comprises an anti-cancer antibody as an active ingredient, said method comprising collecting samples from patients who expresses an antigen which is recognized by the anti-cancer antibody, measuring cadherin function in the samples, and selecting a patient whose the cadherin function is decreased or deleted as a patient to be administered with the pharmaceutical composition which comprises an anti-cancer antibody as an active ingredient;
(16) The method described in the above (15), wherein the cadherin is E-cadherin;
(17) The method described in the above (15) or (16), wherein the patient is a patient with a solid carcinoma;
(18) The method described in any one of the above (15) to (17), wherein the anti-cancer antibody is an antibody against a solid carcinoma;
(19) The method described in any one of the above (15) to (18), wherein the anti-cancer antibody is an anti-PERP antibody;
(20) The method described in any one of the above (15) to (19), wherein the method for measuring cadherin function is a genetic engineering technique or an immunological method;
(21) The method described in the above (20), wherein the immunological method is a method in which an antibody which recognizes cadherin is allowed to react with a sample to thereby measure its reactivity; and
(22) A method for administering a pharmaceutical composition which comprises an anti-cancer antibody as an active ingredient, said method comprising administering the pharmaceutical composition which comprises an anti-cancer antibody as an active ingredient to a patient screened by the method described in any one of the above (1) to (14).

Advantageous Effects of Invention

The present invention provides a method for screening a patient to be administered with a pharmaceutical composition which comprises an anti-cancer antibody as an active ingredient, said method comprising collecting samples from patients who expresses an antigen which is recognized by the anti-cancer antibody, measuring a cadherin function in the samples, and selecting a patient whose the cadherin function is decreased or deleted; a method for screening a patient who has a high efficacy ratio for a pharmaceutical composition which comprises an anti-cancer antibody as an active ingredient; and a method for improving an efficacy ratio for a pharmaceutical composition which comprises an anti-cancer antibody as an active ingredient.

BRIEF DESCRIPTION OF DRAWINGS

FIG. 1 shows a result of examining the antitumor activity of anti-PERP antibody KM3481 in a mouse in vivo model. Names of the cell lines used in the mouse in vivo model are described in respective graphs. The plot shows the average value of V/V0 of each group, and the error bar shows the standard deviation (n=5). The closed circle solid line is a value of the group to which saline was administered, and the open circle solid line is that of the group to which KM3481 was administered. The * shows that the P value is 0.05 or less at respective point of time.

BEST MODE FOR CARRYING OUT THE INVENTION

The present invention provides a method for screening a patient for whom an anti-cancer antibody is more effective due to higher efficacy ratio for the anti-cancer antibody than the conventional cases, by collecting samples from patients who expresses an antigen which is recognized by the anti-cancer antibody, measuring a cadherin function in the samples and selecting a patient whose the original cadherin function in the cancer cell is decreased or deleted.

The cancer according to the present invention is a malignant tumor which develops on the hematopoietic organ, epithelial tissue or non-epithelial tissue, and the cancers that develop on the epithelial tissue or non-epithelial tissue is called solid carcinoma.

The cadherin means a group of molecules having a characteristic amino acid repeating sequence that is called cadherin motif, and a group of molecules having the cadherin motif is called cadherin superfamily.

Cadherin is a functional molecule which is involved in cell-cell adhesion and bonding of cells. Accordingly, the term decrease or deletion of cadherin function as used herein means that the cell-cell adhesion is decreased or deleted as a result of decreasing or deleting the ability of cell adhesion of cadherin.

Examples of the modes of cell-cell adhesion and binding of cells include tight junction, anchoring junction, communicating junction and the like, and examples of the anchoring junction further include adherens junction, desmosome, hemi-desmosome and the like (Molecular Biology of Cells (written in Japanese) $3^{rd}$ edition, edited by Bruce Alberts et al., Tokyo, Kyoikusha (1996), p. 949-1009).

Examples of the cadherin superfamily include a cadherin which functions in the adherens junction, or a cadherin which functions in the desmosome, and the like.

Examples of the cadherin superfamily include E-cadherin (other name cadherin 1), cadherin 2 (N-cadherin), cadherin 3 (P-cadherin), cadherin 4 (R-cadherin), cadherin 5 (VE-cadherin), cadherin 6 (K-cadherin), cadherin 7, cadherin 8, cadherin 9 (T1-cadherin), cadherin 10 (T2-cadherin), cadherin 11 (OB-cadherin), cadherin 12 (N-cadherin 2), cadherin 13 (H-cadherin), cadherin 15 (M-cadherin), cadherin 16 (KSP-cadherin), cadherin 17 (LI-cadherin), cadherin 18, cadherin 19, cadherin 20, cadherin 22, cadherin 23, cadherin 24, cadherin 26 and the like. Among these, E-cadherin is preferred.

Examples of the cadherin which functions in the desmosome include desmoglein-1, desmoglein-2, desmoglein-3, desmoglein-4, desmocollin and the like.

According to the present invention, in order to screen a patient predicting in effectiveness of an anti-cancer antibody, a patient whose the cadherin function is decreased or deleted is firstly screened before administering the anti-cancer antibody, by collecting samples from patients who expresses an antigen which is recognized by the anti-cancer antibody and measuring the cadherin function.

According to the present invention, as the samples of patients who expresses an antigen which is recognized by the anti-cancer antibody, a body fluid, blood, a frozen tissue section, a formalin fixation/paraffin embedding section, a tissue extract and the like can be cited, and DNA and mRNA and the like extracted from these tissues are also included.

The patient according to the present invention is not particularly limited but is preferably a patient having a possibility of generating a cancer, more preferably a patient having a possibility of generating a solid carcinoma. Concrete examples of the solid carcinoma include breast cancer, endometrial cancer, cervical cancer, ovarian cancer, prostatic cancer, bladder cancer, renal carcinoma, gastric cancer, esophageal carcinoma, liver cancer, binary tract cancer, colon cancer, rectal cancer, pancreatic cancer, lung cancer, laryngeal cancer, head and neck cancer, osteosarcoma, thymoma, mesothelioma, melanoma, brain cancer and the like, and metastases accompanied by these primary focal cancers are also included.

As the decrease or deletion of cadherin function, decrease or deletion of cadherin function due to abnormality of expression level of a cadherin molecule, a molecule which cooperates with cadherin or a molecule which controls expression of cadherin, or due to substitution or deletion of amino acids of these protein molecules or abnormality of genes of these molecules, can be cited.

As the abnormality of expression level of a cadherin molecule, a molecule which cooperates with cadherin or a molecule which controls expression of cadherin, decrease of expression of cadherin protein, decrease of expression of a protein which cooperates with cadherin, as a result of the increase or decrease of the protein, and the like can be cited, and the cell adhesion function of cadherin molecules is decreased or deleted by this.

Also, as the abnormality of genes of a cadherin molecule, a molecule which cooperates with cadherin or a molecule which controls expression of cadherin, it includes a case in which expression of the genes is not controlled normally because of the generation of substitution, deletion, or insertion in the sequences of promoter, enhancer, non-translation region and the like on the DNA which is involved in the transcription of mRNA, and the like, and as a result, abnormality of a cadherin molecule, a molecule which cooperates with cadherin or a molecule which controls expression of cadherin is generated.

In addition, as the abnormality of genes of a cadherin molecule, a molecule which cooperates with cadherin or a molecule which controls expression of cadherin, generation of gene mutation such as substitution, deletion or insertion in the DNA which encodes the protein, and the like can be cited, and as a result, addition, deletion or substitution of amino acid is generated in the cadherin molecule or the molecule which cooperates with cadherin so that the cell adhesion function of the cadherin molecule is decreased or deleted.

Regarding the method for measuring the cadherin function of the present invention, in addition to the measurement of the cell adhesion ability of cadherin, a method for measuring expression level, intracellular localization or mutation of the cadherin itself or a molecule which cooperates with cadherin, or abnormality of chromosome coding for the genes of these proteins, and the like can be cited.

Examples of the molecule which cooperates with cadherin include α catenin, β catenin, γ catenin, vinculin, α-actin, plakoglobin, plakophilin, desmoplakin, actin, keratin and the like. Examples of the molecule which controls expression of cadherin include Slug/Snail family, SIP 1 (survival of motor neuron protein interacting protein 1), Twist, ZEB 1 (Zinc finger E-box binding homeobox 1) and the like.

According to the present invention, the measuring method may be any method so long as it is a method for measuring the cadherin function in samples of patients, but specifically, the examples of the measuring method include a method in which the cell adhesion ability of cadherin is measured based on whether or not an aggregation mass of cells is formed when a cancer cell is rotation-cultured using a calcium-containing medium (Science, 251, 1451-4155, 1991). Examples of the method for analyzing the protein or gene of cadherin or a molecule which cooperates with cadherin include an immunological method, a genetic engineering technique and the like, and preferably an immunological method can be used. As the immunological method, an immunohistochemical method in which an antibody which recognizes cadherin is allowed to react with a sample of a patient and its reactivity is measured is preferably used.

As the immunological method, any methods can be included so long as methods which use antigen-antibody reactions, such as an immunoassay, an immunoblotting, an immunoprecipitation reaction aggregation reaction, a complement binding reaction, a hemolysis reaction, an immune gold method, a chromatographic method, or an immunohistochemical method. Among these, an immunohistochemical method can be preferably cited.

Examples of the genetic engineering technique include a RT-PCR method, northern blot method, an in situ hybridization method, a DNA microarray method and the like.

The immunoassay is a method for detecting or determining an antibody or antigen using an antigen or antibody to which certain labeling was applied, and examples include radioimmunoassay (RIA), enzyme immunoassay (EIA or ELISA), fluoroimmunoassay (FIA), luminescent immunoassay, physicochemical detection method, flow cytometry and the like depending on the labeling methods of the antigen or antibody.

As the radioactive label to be used in the radioimmunoassay, any known radioisotope (Koso Men-eki Sokutei Ho (written in Japanese, Enzyme Immunoassay), edited by Eiji Ishikawa et al., published by Igaku Shoin, 1987) can be used. For example, $^{32}P$, $^{125}I$, $^{131}I$ and the like can be used.

As an enzyme label used in the enzyme immunoassay, any known enzymes (Enzyme Immunoassay edited by Eiji Ishikawa, et al., published by Igaku Shoin) can be used. Examples include alkaline phosphatase, peroxidase, luciferase and the like.

As a luminescent label used for luminescent immunoassay, any known luminescents [Bioluminescence and Chemical Luminescence, edited by Kazuhiro Imai, published by Hirokawa Shoten; Rinsho Kensa, 42 (1998)] can be used. Examples include acridinium ester, lophine or the like.

As a fluorescence labeling used in the luminescent immunoassay or flow cytometry, any known fluorescence substances [Immunofluorescent Method, edited by Akira Kawao, published by Soft Science Inc., 1983] can be used. Examples include fluorescence substances, such as FITC, TRITC, PE, CyS, PC5, rhodamine and the like.

As the detection method to be used in the immuno-histochemical method, a detection method which uses an enzyme label or fluorescent label to be used in the enzyme immunoassay or fluoroimmunoassay, a peroxidase-anti-peroxidase complex method, an immune gold method and the like can be cited.

As the physico-chemical method, particle counting immuno assay (PCIA) method, a turbidimetric immuno assay (TIA) method and the like can be cited.

A specific method of the immunohistochemical method is shown in the following.

An antibody which specifically reacts with, cadherin (primary, antibody) is allowed to react with a sample of a patient. Next, expression of cadherin is measured using an antibody (secondary antibody) that specifically reacts with the above-mentioned primary antibody labeled with an enzyme, fluorescence, radioisotope or the like as described above.

Using the above-mentioned measuring method, a patient to be administered with a pharmaceutical composition which comprises an anti-cancer antibody as an active ingredient is screened by selecting a patient in which expression of cadherin is decreased or deleted. More specifically, the patient is screened by the following method.

A cell line or xenograft which shows positive or negative reaction by a cadherin antibody is prepared as a standard sample, and immunohistological staining is carried out on the standard sample and samples obtained from patients. By comparing stained conditions of the cadherin-negative or positive standard sample and the samples obtained from patients, a patient in which a clear staining image is not observed centering at the cell membrane is selected as a patient having decreased or deleted cadherin function, and the said selected patient is regarded as the patient to be administered with a pharmaceutical composition which comprises an anti-cancer antibody as an active ingredient.

Also, by respectively preparing standard samples in which staining of cadherin in a human tissue is negative, weakly positive, positive or strongly positive, a patient having weakly positive or negative staining image in comparison with the standard samples may be selected as a patient having decreased or deleted cadherin expression.

In addition to the above, by preparing the above-described standard samples and patient sample tissues, extracting protein, DNA, mRNA and the like from the tissues and comparing expression of cadherin in the standard samples and patient samples, a patient whose cadherin expression level is decreased in comparison with the standard samples may be regarded as a patient having decreased or deleted cadherin expression.

After selecting patients whose cadherin function is decreased or deleted, by the method exemplified in the above, these patients are regarded as the patients to be administered with a pharmaceutical composition which comprises an anti-cancer antibody as an active ingredient, and the pharmaceutical composition is administered thereto. By this administration method, an efficacy ratio for the pharmaceutical composition which comprises an anti-cancer antibody as an active ingredient can be improved.

The antibody of the present invention includes an antibody, a fragment of the antibody and derivatives thereof, and forms and action mechanisms of the molecules are not limited.

The antibody of the present invention includes a polyclonal antibody and a clonal antibody, and preferably a monoclonal antibody is used.

The monoclonal antibody includes an antibody produced by a hybridoma and a recombinant antibody produced by a transformant transfected with an expression vector containing a gene encoding an antibody.

The recombinant antibody includes antibodies prepared by gene recombination, such as a humanized antibody, a human antibody or an antibody fragment.

The humanized antibody of the present invention includes a human chimeric antibody and a human CDR-grafted antibody.

The human chimeric antibody is an antibody con rising a heavy chain variable region (hereinafter referred to as "VH")

and a light chain variable region (hereinafter referred to as "VL") from a non-human animal, and a heavy chain constant region (hereinafter referred to as "CH") and a light chain constant region (hereinafter referred to as "CL") from a human antibody.

The human CDR-grafted antibody is an antibody in which CDR amino acid sequences of VH and VL of an antibody from a non-human animal are grafted into appropriate positions of VH and VL of a human antibody.

A human antibody is originally an antibody naturally existing in the human body, but it also includes antibodies obtained from a human antibody phage library, a human antibody-producing transgenic animal, which are prepared based on the recent advance in genetic engineering, cell engineering and developmental engineering techniques.

The antibody naturally existing in the human body can be prepared, for example, by isolating a human peripheral blood lymphocyte, immortalizing by infecting with EB virus or the like and then cloning it to thereby obtain lymphocytes capable of producing the antibody, culturing the lymphocytes thus obtained, and purifying the antibody from the culture.

The human antibody phage library is a library in which antibody fragments such as Fab and scFv are expressed on the phage surface by inserting a gene encoding an antibody gene prepared from a human B cell into a phage gene. A phage expressing an antibody fragment having the desired antigen binding activity on the surface can be recovered from the library, using the binding activity to an antigen-immobilized substrate as the index. The antibody fragment can be converted further into a human antibody molecule comprising two full length H chains and two full length L chains by genetic engineering techniques.

A human antibody-producing transgenic animal is an animal in which a human antibody gene is integrated into its cells. Specifically, a human antibody-producing transgenic mouse can be prepared by introducing a human antibody gene into ES cell of a mouse, transplanting the ES cell into an early stage embryo of other mouse and then developing it. A method for producing a human antibody from a human antibody-producing transgenic animal comprises obtaining a human antibody-producing hybridoma by a hybridoma preparation method usually carried out in non-human animals, culturing the obtained hybridoma and accumulating the human antibody in the culture supernatant.

The antibody fragment of the present invention includes Fab, F(ab')$_2$, Fab', scFv, diabody, dsFv, a peptide comprising CDR, and the like.

An Fab is an antibody fragment having a molecular weight of about 50,000 and having antigen binding activity, in which about a half of the N-terminal side of H chain and the entire L chain, among fragments obtained by treating IgG with a protease, papain (cleaving an amino acid residue at the 224th position of the H chain), are bound together through a disulfide bond.

An F(ab')$_2$ is an antibody fragment having a molecular weight of about 100,000, having antigen binding activity and comprising two Fab regions which are bound in the hinge position obtained by digesting the lower part of two disulfide bonds in the hinge region of IgG, with enzyme, pepsin.

An Fab' is an antibody fragment having a molecular weight of about 50,000 and having antigen binding activity, which is obtained by cleaving a disulfide bond at the hinge region of the F(ab')$_2$.

An scFv is a VH-P-VL or VL-P-VH polypeptide in which one chain VH and one chain VL are linked using an appropriate peptide linker (hereinafter referred to as "P") and is an antibody fragment having antigen binding activity.

A diabody is an antibody fragment in which scFv's forms a dimer, and has divalent antigen binding activity, in the divalent antigen binding activity, two antigens may be the same or different.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. (Protein Engineering, 7, 697 (1994)).

A peptide comprising CDR is constituted by including one region or more of CDRs of VH or VL. Plural peptide comprising CDRs can be bound directly or via an appropriate peptide linker. The peptide comprising CDR can also be produced by a chemical synthesis method such as an Fmoc method (fluorenylmethoxycarbonyl method) or a tBoc method (t-butyloxycarbonyl method), or the like.

The anti-cancer antibody according to the present invention is not limited to a specific action mechanism so long as it is an antibody against a cancer. As the action mechanism of an anti-cancer antibody, antibody-dependent cellular cytotoxicity (hereinafter referred to as ADCC activity), complement-dependent cytotoxicity (hereinafter referred to as CDC activity) and the like can be cited. The ADCC activity is the activity to antibody-dependently cause damage on cancer cells via immunocyte in the living body. The CDC activity is the activity to cause damage on cancer cells via a complement in the living body.

The action mechanism of the anti-cancer antibody of the present invention may be an activity to modify function of an antigen by binding of the antibody against the antigen. The anti-cancer antibody having the activity to modify function of an antigen by binding of the antibody against the antigen includes an antibody which inhibits proliferation and survival of a cancer cell by modifying the natural physiological activity of the antigen through the antigen-antibody reaction, and the like.

The derivatives of the antibody of the present invention or a fragment of the antibody may be derivatives in which a substance having cytotoxicity is covalently bound to the antibody, derivatives in which a molecule which binds to a substance having cytotoxicity by intermolecular force bond is covalently bound to the antibody, derivatives in which a prodrug having cytotoxicity is covalently bound and the like.

The substance having cytotoxicity may be any substance so long as It is a substance which has the ability to injure a cancer cell. Preferably, a radioisotope, a protein, a chemotherapeutic and the like can be cited.

Examples of the radioisotope having potential ability to injure a cancer cell include $^{131}$I, $^{125}$I, $^{90}$Y, $^{64}$Cu, $^{99}$Tc, $^{77}$Lu, $^{211}$At and the like.

As an example of the protein which has the ability to indirectly injure a cancer cell making use of the patient's immune system, a cytokine that activates immuno-competent cells is suitable, and examples include human interleukin 2 (hIL-2), human granulocyte macrophage colony-stimulating factor (hGM-CSF), human macrophage colony-stimulating factor (hM-CSF), human interleukin 12 (hIL-12) and the like. In addition, ricin, auristatin, diphtheria toxin and the like toxins which directly injure cancer cells can also be used.

Examples of the chemotherapeutic having the ability to injure cancer cells include anticancer agents, for example, alkylating agents, such as nitrogen mustard, and cyclophosphamide; metabolic antagonists, such as 5-fluorouracil, methotrexate; antibiotics, such as daunomycin, bleomycin, mitomycin C, daunorubicin, and doxorubicin; plant alkaloids, such as vincristine, vinblastine, and vindesine; hormones, such as tamoxifen, and dexamethasone; platinum preparations, such as cisplatin; Maytansinoid and derivatives thereof, and the like [Rinsho Shuyo Gaku (written in Japanese, Clinical Tumor Science), edited by Japan Society of Clinical Tumor, published by Gan to Kagaku Ryoho (1982)], anti-inflammatory agents, for example, non-steroidal preparations, such as hydrocortisone, and prednisone; steroidal preparations, such as aspirin, and indometacin; immunomodulators, such as aurothiomalate, and penicillamine; immunosuppressants, such as cyclophosphamide, and azathioprine; antihistaminics, such as chlorphenylamine maleate, and clemastine; and the like [Inflammation and Anti-inflammatory Therapy (written in Japanese), Ishiyaku Shuppan (1982)] and the like.

Specific examples of the molecule which binds to a substance having cytotoxicity which has the ability to injure cancer cells by intermolecular force bond include methylbenzyldiethylene-triaminepentaacetic acid (MX-DTPA).

Examples of the prodrug having cytotoxic activity include valganciclovir, aciclovir, irinotecan, tegafur and the like.

According to the present invention, the antigen which is recognized by the anti-cancer antibody may be any antigen and not limited to a specific antigen, so long as it is expressed on the surface of cancer cell.

Examples include a four-transmembrane membrane protein, a cytokine which is expressed on the cell membrane, a growth factor, a receptor of a cytokine or chemokine, a cluster of differentiation antigen (CD antigen), an immune regulatory protein, a transporter, an adhesion-related molecule, a carcinoembryonic antigen, a sugar chain, a membrane protein, a ganglioside, a cytokine or chemokine bound to a sugar chain or glycoprotein on the surface of a cancer cell membrane.

The four-transmembrane protein expressing on a cancer cell membrane may be any molecule which has a characteristic of being expressed on the surface of a cancer cell, and the molecule may be a molecule of any function. Specific examples of the molecule include CD20, CD81, D6.1A/CO-029/TM4SF3, CD63 (HOP-26, LAMP-3), tetraspanin-5 (Tspan-5, Tm4sf9), CD82 (KAI1), CD151 (PETA-3/SFA-1), CDR (MRP-1), SDTM4SF, peripherin-2 (peripherin/rds), CD53 (panleukocyte Ag), OSP/claudin-11 (OAP-1,Tspan-3), KAI1 COOH-terminal interacting tetraspanin (KITENIN), CD37, T-cell acute lymphoblastic leukemia antigen-1 (TALLA-1), CO-029, TM4SF5 (transmembrane 4 superfamily, member 5), ROM-I (rod outer segment membrane protein 1), new EST tetraspan (NET-1, -2, -3, -4, -5, -6, -7), TSSC6 (Phemx), MP20, Tspan-5, TM4SF4 (iI-TMP), TM4-B, divalent metal transporter (DMT1), stargazin (TARP), occludin, myelin and lymphocyte protein (MAL), claudin family (CLDN-1, -2, -3, -4, -5, -7, -8, -9, -10, -11, -12, -16, -18), claudin like protein of 24 kDa (CLP24), peripheral myelin protein (PMP22), p53 apoptosis effector related to PMP22 (PERP), growth arrest specific 3 (gas3), PASII, connexin, Epiyherial membrane protein-2 (EMP2), plasmolipin, brain cell membrane protein 1 (BCMP1), platelet-endothelial tetraspan antigen 3 (PETA-3), oligodendrocyte-specific protein (OSP), sarcospan (SPN), MVP17 (rMAL, VIP17, MAL), uroplakin 1B (UPK1B), connexin32 (Cx32), TAPA-1 (target of the antiproliferative antibody 1), NAG-2, *C. perfringens* enterotoxin receptor (CPE-R) and ART-1 (AML1-regulated transmembrane protein 1) and the like.

Examples of the cytokine which expresses on a cell membrane include a cytokine which is synthesized as transmembrane protein, a cytokine in which its Latent type before undergoing posttranslational modification of protein is bound to the surface of a cell, and the like.

Examples of the cytokine which expresses on a cell membrane include TNFα (tumor necrosis factor alpha), HB-EGF (heparin binding-EGF like growth factor), TNFβ, CD40 ligand, OX40 ligand, CD70, RANKL (receptor activator of nuclear factor kappa B ligand), TRAIL (TNF-related apoptosis-inducing ligand receptor), FAS ligand, TWEAK, IL-1α, IL-1β, lymphotactin, CD30 ligand, 4-1BB ligand and the like.

Examples of the cytokine having a property in which its Latent type before undergoing posttranslational modification of protein binds to the surface of a cell include TGF β family and the like.

The receptor of a growth factor may be any substance so long as it is a protein on the surface of a cell membrane, which receives a signal of the growth factor. Examples of the receptor of a growth factor include human EGF receptor 1 (HER1), HER2, HER3, HER4, insulin receptor, insulin-like growth factor I receptor (IGF-IR), IGF-IIR, insulin receptor related receptor, platelet derived growth factor receptor (PDGFR) a, PDGFRss, CSFIR, c-kit, c-fms, fetus liver kinase receptor, VEGFR1 (Flt-1), VEGFR2 (KDR), VEGFR3 (Flt-4), fibroblast growth factor (FGF) receptor group, FGFR1, FGFR2, FGFR3 FGFR4 and the like.

The receptor of a cytokine may be any substance so long as it is a protein on the surface of a cell membrane, which receives a signal of the cytokine. Examples of the receptor of a cytokine include Epo (erythropoietin), IL-2, IL-3, IL-4, IL-5, IL-6, IL-7, IL-9, IL-11, IL-13, G-CSF (granulocyte colony stimulating factor), IL-15, GM-CSF (granulocyte-macrophage colony stimulating factor), OSM (oncostatin M), LIF (leukemia inhibitory factor), IFNγ (interferon-gamma), IFNα, IFNγ, INFβ, TGFβ (transforming growth factor beta), IL-1α, IL-1β, IL-1RA, IL-10, IL-12, MIF (macrophage migration inhibitory factor), IL-16, IL-17, IL-18, IL-23 and the like.

The receptor of a chemokine may be any substance so long as it is a protein on the surface of a cell membrane, which receives a signal of the chemokine. Examples of the receptor of a chemokine include CCR1 (chemokine (C-C motif) receptor 1), CCR2, CCR3, CCR4, CCR5, CCR6, CCR7, CCR8, CCR9, CCR10, CXCR1 (chemokine (C—X—C motif) receptor), CXCR2, CXCR3, CXCR4, CXCR5, CXCR6, XCRI (chemokine (C motif) receptor 1), CX3CR1 (chemokine (C-X3-C) receptor 1) and the like.

The CD antigen may be any substance so long as it is expressed in a cancer cell, and for example, a CD antigen which is expressed in an epithelial-like cell can be cited. Examples of the CD antigen include CD1, CD9, CD10, CD13, CDw17, CD21, CD24, CD26, CD29, CD39, CD40, CD44, CD46, CD47, CD52, CD55, CD58, CD60, CD66, CD73, CD74, CD75, CD77, CD81, CD88, CD91, CD92, CD98, CD99, CD104, CD109, CD110, CD111, CD112, CDw113, CD116, CD118, CD120, CD124, CD129, CD133, CDw136, CDw137, CD138, CD142, CD143, CDw145, CD151, CD164, CD165, CD166, CD167, CD174, CD175, CD176, CD178, CD224, CD227, CD234, CD239, CD249, CD295, CD296, CD324, CD326, CD331, CD332, CD333, CD334, CD339 and the like.

The immune regulatory protein may be any substance so long as it is a protein on the surface of a cancer cell membrane, which regulates immunity. Examples include are a protein which transmits a sign-al directly to a cell involved in immunity and thereby regulates function of the cell and a protein that indirectly regulates function of an immunocyte by acting upon a microenvironment in the living body. Examples of the immune regulatory protein include HLA-A (human leukocyte antigen-A), HLA-B, HLA-C, HLA-DP, HLA-DQ, HLA-DR, HLA-E, HLA-F, HLA-G, MIC-A, MIC-B, HLA-DO, B7.1, B7.2, B7-H1, B7-H2, B7-DC, B7-H3, B7-H4, Adenosin deaminase, dipeptidyl peptidase IV, ADAM (a disintegrin and metalloproteinase domain) family, fibroblast activationprotein (FAP), RCAS-1, Thioredoxin and the like.

The transporter may be any substance so long as it is a protein on the surface of a cell membrane, which carries out transportation of intracellular and extracellular ions and organic substances via cell membrane. Examples include two transporters of the ABC (ATP binding cassette) family which carries out transportation making use of the energy of ATP and the SLC (Solute carrier) family that carries out transportation without using the energy of ATP, and either one may be the transporter of the present invention.

Examples of the ABC transporter include MRP1 (Multidrug resistance-associated protein 1, other name: ATP-binding cassette sub-family C member 1 (ABCC1)), MRP2 (ABCC2), MRP3 (ABCC3), MRP4 (ABCC4), MRP5 (ABCC5), MRP6 (ABCC6), MRP8 (ABCC8), MRP9 (ABCC9), MRP10 (ABCC10), MRP11 (ABCC11), MRP12 (ABCC12), MRP13 (ABCC13), MXR, MDR1 (Multidrug resistance protein 1, other name: ATP-binding cassette sub-family B member 1 (ABCB1)), MDR4 (ABCB4), MDR5 (ABCB5), MDR6 (ABCB6), MDR7 (ABCB7), MDR8 (ABCB8), MDR9 (ABCB9), MDR10 (ABCB10), MDR11 (ABCB11) and the like.

Examples of the SLC transporter include SLC1A1, SLC1A2, SLC1A3, SLC1A4, SLC1A5, SLC1A6, SLC1A7, SLC7A1, SLC7A2, SLC7A3, SLC7A4, SLC7A5, SLC7A6, SLC7A7, SLC7A8, SLC7A9, SLC7A10, SLC7A11, SLC7A12, SLC7A13, SLC7A14 and the like.

The antigen of adhesion-related molecule may be any molecule so long as it is a molecule which expresses on the surface of a cancer cell and is involved in cell adhesion. Examples of the antigen of adhesion-related molecule include collagen family molecule, fibronectin, vitronectin, selectin family molecule, integrin family molecule, laminin, tenascin, VCAM (vascular cell adhesion molecule), EpCAM, ICAM, IgCAM, ALCAM, MAdCAM, NCAM, GlyCAM, CEA and the like.

The sugar chain antigen may be any substance so long as it is a sugar chain which is specifically high-expressed in a cancer cell. Examples of the sugar chain antigen include T antigen, Tn antigen, sialyl T antigen, sialyl Tn antigen, GalNAc-T1, GalNAc-T2, GalNAc-T3, GalNAc-T4, Le$^a$ antigen, sialyl-Le$^a$ antigen, Le$^x$ antigen, sialyl-Le$^x$ antigen, Le$^y$ antigen and the like.

Examples of the ganglioside include GD1a, GD1b, GD2, GD3, GM1, GM2, GM3, GT1b, GQ1b and the like.

Examples of the sugar protein include mucin-1, mucin-2, mucin-3, mucin-4, mucin-5AC, mucin-5B, mucin-6, mucin-11/12, mucin-16, mucin-17 and the like.

The cytokine or chemokine which binds to a sugar chain or glycoprotein on the surface of a cancer cell membrane may be any substance so long as the cytokine or chemokine can be recognized as an antigen of the cell surface by binding to the sugar chain or glycoprotein on the surface of cancer cell membrane.

Examples of the cytokine or chemokine which binds to a sugar chain or glycoprotein on the surface of a cancer cell membrane include FGF family molecule, PDGF, BMP (bone morphogenetic protein), GM-CSF, HGF (hepatocyte growth factor), HB-EGF, neuregulin-1, amphiregulin and the like.

Examples of the chemokine which binds to a sugar chain or glycoprotein on a cancer cell membrane include a chemokine which has an amino acid sequence BBXB or BXBXXB as a glycosaminoglycan binding motif on the surface of a cell membrane. The B of BBXB represents a basic amino acid, and X may be any amino acid. Examples of the chemokine which has the above glycosaminoglycan binding motif include CXCL12, CCL3, CCL4, CCL5, CXCL8, CCL2, XCL1 and the like.

As the route of administration of a pharmaceutical composition which comprises the above-described anti-cancer antibody as an active ingredient, it is desirable to use those which are most effective in carrying out the treatment, such as oral administration or buccal, nasal, tracheal, rectal, subcutaneous, intramuscular, intraperitoneal, intravenous and the like parenteral administration, and in the case of an antibody or peptide preparation, intravenous administration can be desirably cited. The dosage form includes sprays, capsules, tablets, granules, syrups, emulsions, suppositories, injections, ointments, tapes and the like.

The pharmaceutical preparation suitable for oral administration includes emulsions, syrups, capsules, tablets, powders, granules and the like. Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like. Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like. Injections can be prepared using a carrier such as a salt solution, a glucose solution or a mixture of both thereof. Suppositories can be prepared using a carrier such as cacao butter, hydrogenated fat or carboxylic acid. Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. Depending on the properties of the antibody and the carrier, it is possible to produce pharmaceutical preparations such as aerosols and dry powders. In addition, the components exemplified as additives for oral preparations can also be added to the parenteral preparations.

Although the dose or the frequency of administration varies depending on the objective therapeutic effect, administration, method, treating period, age, body weight and the like, it is usually 10 μg/kg to 8 mg/kg per day and per adult.

The present invention is explained below in detail based on Examples; however, the present invention is not limited to the following Examples.

EXAMPLES

Example 1

In order to examine the antitumor activity of an anti-cancer antibody, effect of the anti-cancer antibody in a mouse in vivo model was examined. As the mouse in vivo model, a mouse in which a human cancer cell was subcutaneously transplanted was used and the effect was judged using the volume of the tumor grown subcutaneously as the index.

A cell suspension of a human cancer cell line AsPC-1 (ATCC No. CRL-1682), Capan-2 (ATCC No. HTB-80), CFPAC-1 (ATCC No. CRL-1918). HPAC (ATCC No. CRL-2119), KP-3L (JCRB 0178.1), MIA PaCa-2 (ATCC No. CRL-1420), Hep G2 (ATCC No. HB-8065), Calu-3 (ATCC No. HTB-55), MEC (TKG 0629, Cell resource Center for Biomedical Research attached to Institute of Development, Aging and Cancer, Tohoku University) or IHGGK (TKG 0623, Cell resource Center for Biomedical Research attached to Institute of Development, Aging and Cancer, Tohoku University) maintained by in vitro subculture, or a tumor tissue section of a human cancer cell PANG-1 (ATCC No. CRL-1469) or Li-7 (Central Institute for Experimental Animal) maintained by in vivo subculture, was transplanted into the abdominal side of male SCID mice (CLEA Japan). In order to increase the growing ability of the tumor cell in response to the necessity of each cell line, the mice were subjected to an intraperitoneal pretreatment with 20 µl per animal of anti-Asialo GM1 antibody (manufactured by by Wako Pure Chemical Industries) or to a pretreatment of whole body irradiation of X-rays (250 Rad), 3 to 4 days before the cancer cell transplantation.

After 10 to 25 days of the cancer cell transplantation, individuals which growth of the cancer cell was confirmed were selected and groups were organized in such a manner that the tumor volume did not vary among groups. The number of examples was set to 2 to 5 per group. Saline (manufactured by by Otsuka Pharmaceutical) for the control group, or a human-mouse chimeric anti-p53 apoptosis effector related to PMP 22 (PERP) antibody KM3481 (WO 2005/121338A1) for the antibody administration group, was administered into mouse tail vein at a dose of 1 mg/kg, twice a week, for 3 to 4 weeks. In the case of the control group, the treatment was not carried out or saline was administered.

Figure 1:
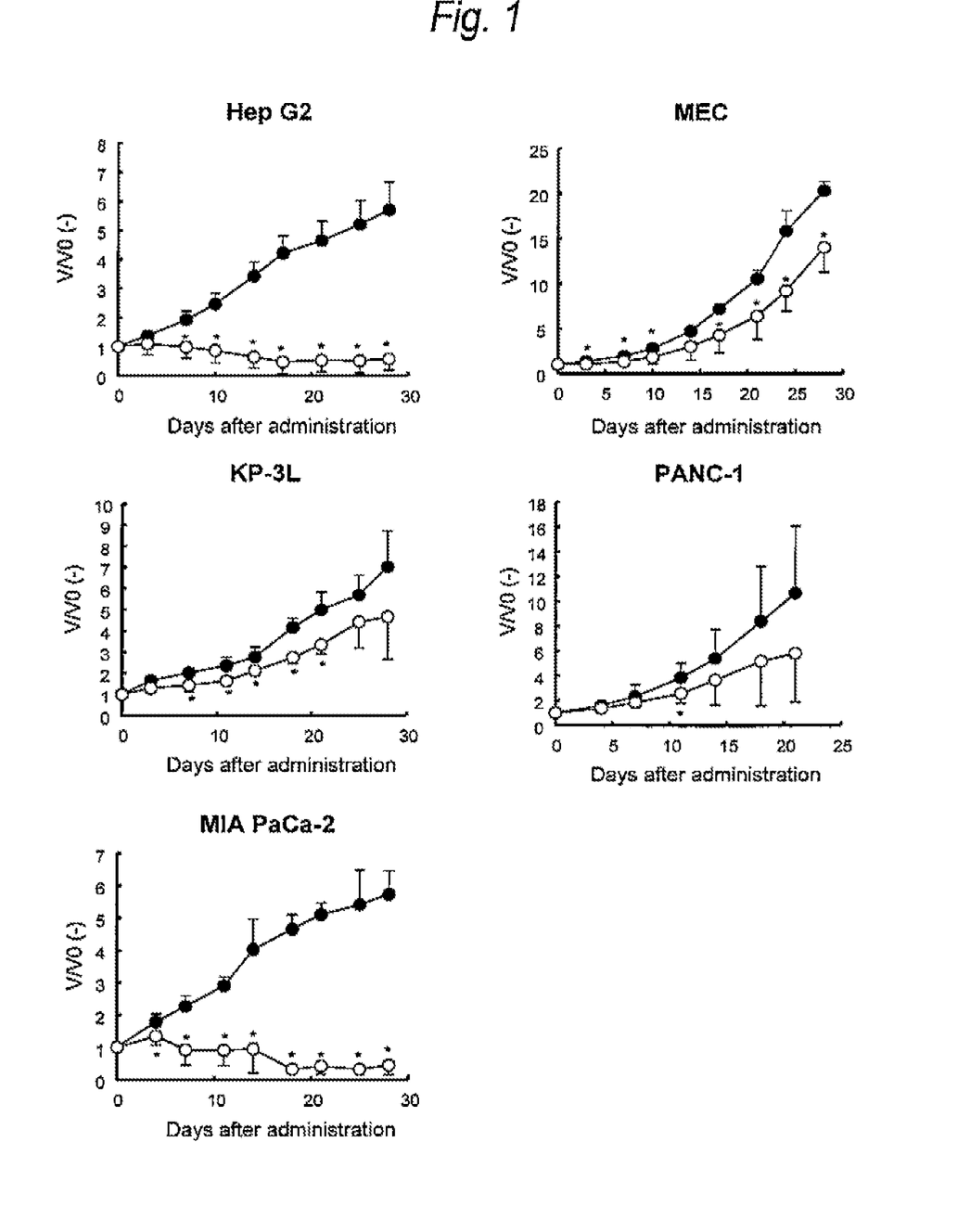
Figure 2:
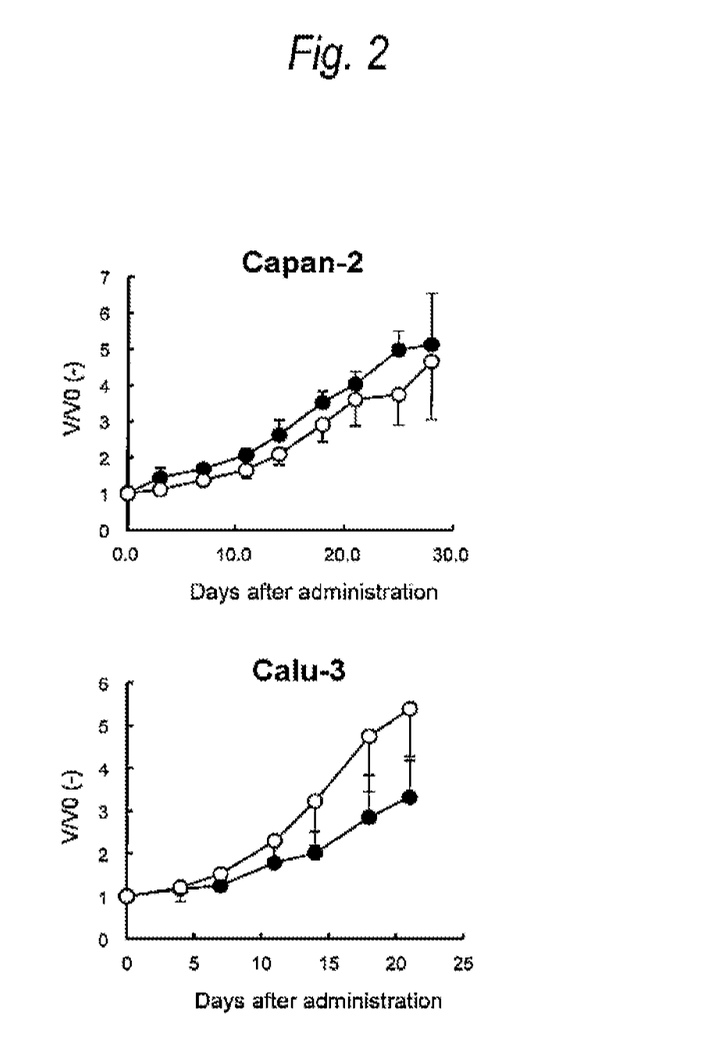
FIG. 2 shows a result of examining the antitumor activity of anti-PERP antibody KM3481 in a mouse in vivo model. Names of the cell lines use in the mouse in vivo model are described in respective graphs. The plot shows the average value of V/V0 of each group, and the error bar shows the standard deviation, (n=5). The closed circle solid line is a value of the group to which saline was administered, and the open circle solid line is that of the group to which KM3481 was administered.
Figure 3:
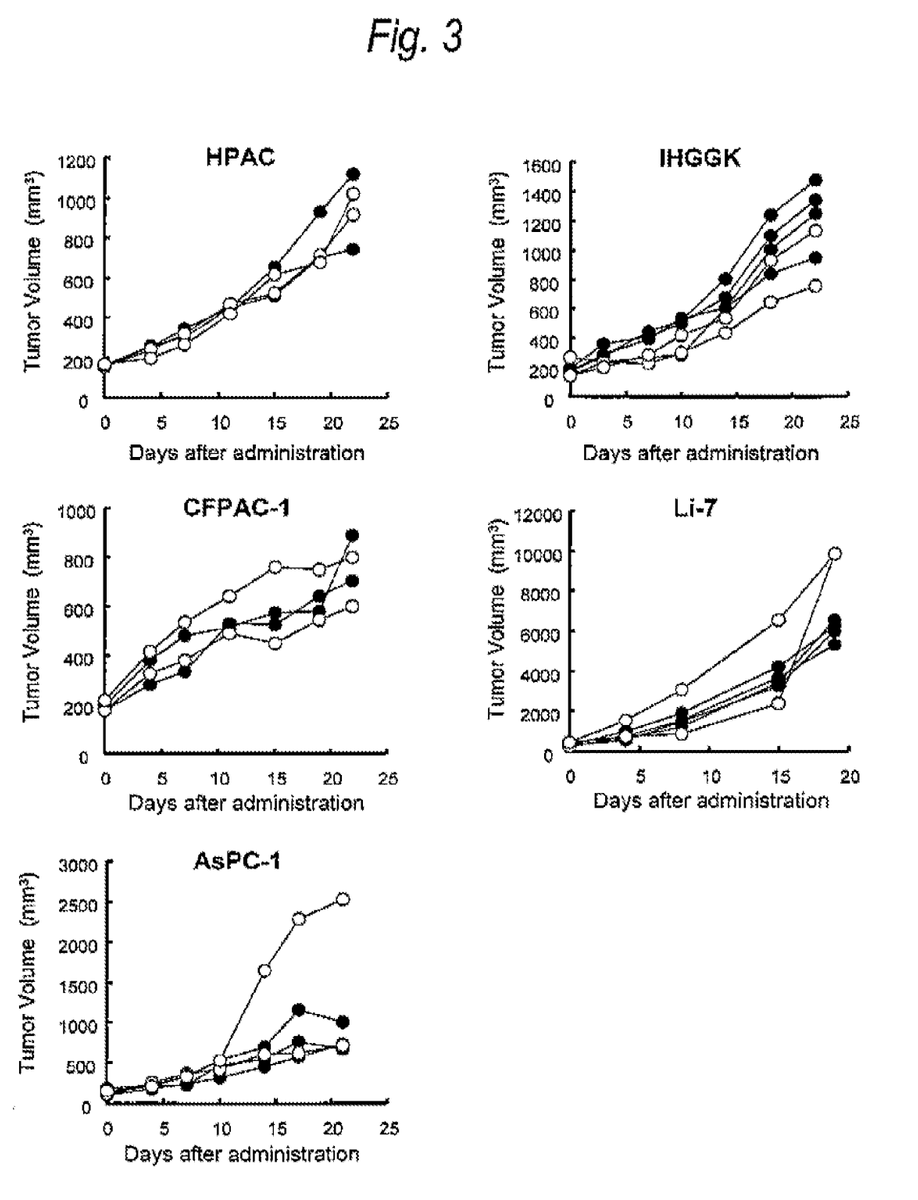
FIG. 3 shows a result of examining the antitumor activity of anti-PERP antibody KM3481 in a mouse in viva model. Names of the cell lines used in the mouse in vivo model are described in respective graphs. The plot shows the value of tumor volume of each individual. The closed circle solid line is a value of the untreated mouse, and the open circle solid line is that of the mouse to which KM3481 was administered.

The tumor volume was measured on the day of the antibody administration. The length and breadth of the tumor were measured and substituted for Formula 1 to calculate the tumor volume. The tumor volume on the day of the commencement of administration was regarded as V0, and the tumor volume on the day of each measurement as V, and the ratio of V and V0 (V/V0) was calculated for each individual. In the test in which the number of examples per group was constituted by 5, the value of V/V0 was used in a statistical analysis. The statistical analysis was carried out using a statistical analysis software SAS (SAS Institute). When the P value was 0.05 or less, it was judged that the difference was significant.

tumor volume (mm$^3$)=length (mm)×breadth (mm)× breadth (mm)×0.5    Formula 1:

In the mouse model of MIA PaCa-2, PANC-1, KP-3L, MEC or Hep G2, tumor volume of the group to which the anti-PERP antibody KM3481 was administered was statistically significantly small in comparison with the group to which saline was administered. Accordingly, it was found that the anti-PERP antibody has antitumor activity for the tumors of MIA PaCa-2, PANC-1, KP-3L, MEC and Hep G2 (FIG. 1). On the other hand, no antitumor activity of KM3481 for Calu-3 and Capan-2 (FIG. 2) and HPAC, CFPAC-1, AsPC-1, IHGGK and Li-7 (FIG. 3) was found.

Example 2

Next, expressions of E-cadherin which is involved in cell adhesion and PERP which is recognized by the anti-PERP antibody KM3481 were analyzed by an immuno-histological staining method. Respective tumor tissues grown subcutaneously of mice were collected from mouse individuals to which the anti-PERP antibody KM3481 was not administered. Tumor tissue pieces without necrosis were cut out and embedded in O.C.T. Compound (manufactured by by Sakura Finetek Japan). The tumor tissues embedded in O.C.T. Compound were frozen with liquid nitrogen to obtain frozen tissues. Sections were prepared from each frozen tissue using a cryostat. PERP staining specimens were prepared using biotin-labeled ant-PERP antibody KM3481 and streptavidin HRP (manufactured by by DAKO). Also, E-cadherin staining specimens were prepared using anti-E-cadherin antibody (manufactured by by DAKO) and ENVISION+ (manufactured by by DAKO).

The prepared samples were observed under a light microscope and the reactivity of the antibody was evaluated based on the four grades of negative (−), weakly positive (±), moderately positive (+) and strongly positive (++), with the results shown in Table 1.

TABLE 1

Expression of PERP and Cadherin

| Cell | PERP* | E-cadherin* |
|---|---|---|
| AsPC-1 | ++ | ++ |
| Capan-2 | ++ | ++ |
| CFPAC-1 | ++ | ++ |
| HPAC | ++ | ++ |
| KP-3L | ++ | ++ |
| MIA PaCa-2 | ± | − |
| Hep G2 | + | + |
| Calu-3 | ++ | ++ |
| MEC | + | − |
| IHGGK | ++ | ++ |
| PANC-1 | ++ | − |
| Li-7 | + | + |

*++ strongly positive, + moderately positive, ± weakly positive, − negative

As shown in Table 1, expression of PERP was found in all of the measured cell lines, namely AsPC-1, Capan-2, CFPAC-1, HPAC, KP-3L, MIA PaCa-2, Hep G2, Calu-3, MEC, IHGGK, PANC-1 and Li-7.

On the other hand, expression of E-cadherin was found in AsPC-1, Capan-2, CFPAC-1, HPAC, KP-3L, Hep G2, Calu-3, IHGGK and Li-7 but was not found in MIA PaCa-2, MEC and PANC-1.

Example 3

By carrying out examination on the correlation between the presence or absence of expression of E-cadherin and the efficacy of anti-PERP antibody KM3481, shown in Examples 1 and 2, a categorical contingency table was prepared (Table 2) regarding the presence or absence of the antitumor activity of anti-PERP antibody KM3481 and expression of E-cadherin. Names of the cell lines belonging to the respective categories are shown in the table.

TABLE 2

|  |  | Expression of E-cadherin | |
|---|---|---|---|
|  |  | Positive | Negative |
| Efficacy | Positive | KP-3L<br>Hep G2 | PANC-1<br>MIA PaCa-2<br>MEC |
|  | Negative | AsPC-1 |  |

TABLE 2-continued

| | Expression of E-cadherin | |
|---|---|---|
| | Positive | Negative |
| | Capan-2 | |
| | CFPAC-1 | |
| | HPAC | |
| | IHGGK | |
| | Li-7 | |
| | Calu-3 | |

In addition, whether or not the frequency of the onset of the efficacy of the anti-PERP antibody KM3481 on E-cadherin positive cell lines is high in comparison with the onset of the efficacy of the anti-PERP antibody 1KM3481 for E-cadherin negative cell lines was statistically analyzed by the Fisher's direct probability calculation method. When the P value was 0.05 or less, it was judged that the difference was significant.

As a result, the probability of confirming the efficacy of the anti-PERP antibody against E-cadherin negative cell lines was 100%, and on the other hand, the probability of confirming the efficacy of the anti-PERP antibody against E-cadherin positive cell lines was 22%. That is, the efficacy of the anti-PERP antibody was found in all of the E-cadherin negative 3/3 cell lines, and the efficacy of anti-PERP antibody was found in the E-cadherin positive 2/9 cell lines. Accordingly, since the P value calculated by the Fisher's direct probability calculation method was 0.455, it was revealed that the difference in probability of finding the efficacy of the anti-PERP antibody is a significant difference.

Based on the above results, it was found that the efficacy ratio for an antibody against a cancer antigen expressing in cancer cells of patients can be increased by selecting a patient whose E-cadherin expression is decreased or deleted.

While the present invention has been described in detail and with reference to specific embodiments thereof, it will be apparent to one skill in the art that various changes and modifications can be made therein without departing from the sprit and scope thereof.

This application is based on U.S. Provisional Application No. 60/946,278 filed on Jun. 26, 2007, the entire contents of which are incorporated hereinto by reference. All references cited herein are incorporated in their entirety.

INDUSTRIAL APPLICABILITY

The present invention provides a method for screening a patient to be administered with a pharmaceutical composition which comprises an anti-cancer antibody as an active ingredient, said method comprising collecting samples from patients who expresses an antigen which is recognized by the anti-cancer antibody, measuring cadherin function in the samples, and selecting a patient whose the cadherin function is decreased or deleted; a method for screening a patient who has a high efficacy ratio for a pharmaceutical composition which comprises an anti-cancer antibody as an active ingredient; and a method for improving an efficacy ratio for a pharmaceutical composition which comprises an anti-cancer antibody as an active ingredient.

The invention claimed is:

1. A method for improving an efficacy ratio for a pharmaceutical composition against a primary focal cancer, wherein said pharmaceutical composition comprises an anti-cancer antibody that recognizes a cell-surface antigen as an active ingredient, and wherein said method comprises collecting samples from patients suspected of having a primary focal cancer who express the cell-surface antigen recognized by the anti-cancer antibody; measuring E-cadherin function or expression, or both, in the samples; selecting a patient in whose sample the E-cadherin function or expression is decreased or deleted as a patient to be administered said pharmaceutical composition; and administering the pharmaceutical composition to the selected patient.

2. The method according to claim 1, wherein the patient is a patient with a solid carcinoma.

3. The method according to claim 1, wherein the anti-cancer antibody is an antibody against a solid carcinoma.

4. The method according to claim 1, wherein the anti-cancer antibody is an anti-PERP antibody.

5. The method according to claim 1, wherein the method for measuring the E-cadherin function is a genetic engineering technique or an immunological method.

6. The method according to claim 5, wherein the immunological method is a method in which an antibody which recognizes E-cadherin is allowed to react with a sample to thereby measure its reactivity.

7. A method for screening patients suspected of having a primary focal cancer to select a patient to be administered a pharmaceutical composition, wherein said pharmaceutical composition comprises an anti-cancer antibody that recognizes a cell-surface antigen as an active ingredient,
said method comprising collecting samples from patients suspected of having a primary focal cancer who express the cell-surface antigen recognized by the anti-cancer antibody; measuring E-cadherin function or expression, or both, in the samples; selecting a patient in whose sample the E-cadherin function or expression is decreased or deleted as a patient to be administered said pharmaceutical composition; and administering the pharmaceutical composition to the selected patient.

8. A method for screening patients suspected of having a primary focal cancer to select a patient who has a high efficacy ratio for a pharmaceutical composition against a primary focal cancer, wherein said pharmaceutical composition comprises an anti-cancer antibody that recognizes a cell-surface antigen as an active ingredient, and wherein said method comprises collecting samples from patients suspected of having a primary focal cancer who express the cell-surface antigen recognized by the anti-cancer antibody; measuring E-cadherin function or expression, or both, in the samples; selecting a patient in whose sample the E-cadherin function or expression is decreased or deleted as a patient having a high efficacy ratio for said pharmaceutical composition; and administering the pharmaceutical composition to the selected patient.

9. The method according to claim 7 or 8, wherein the patient is a patient with a solid carcinoma.

10. The method according to claim 7 or 8, wherein the anti-cancer antibody is an antibody against a solid carcinoma.

11. The method according to claim 7 or 8, wherein the anti-cancer antibody is an anti-PERP antibody.

12. The method according to claim 7 or 8, wherein the method for measuring the E-cadherin function is a genetic engineering technique or an immunological method.

13. The method according to claim 12, wherein the immunological method is a method in which an antibody which recognizes E-cadherin is allowed to react with a sample to thereby measure its reactivity.

* * * * *